United States Patent
Driscoll

(10) Patent No.: US 10,052,352 B2
(45) Date of Patent: *Aug. 21, 2018

(54) THERAPEUTIC APPLICATION OF PARENTERAL KRILL OIL

(75) Inventor: David F. Driscoll, Bridgewater, MA (US)

(73) Assignee: STABLE SOLUTIONS LLC, Goleta, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/126,807

(22) PCT Filed: Jun. 13, 2012

(86) PCT No.: PCT/IB2012/001156
§ 371 (c)(1),
(2), (4) Date: Dec. 16, 2013

(87) PCT Pub. No.: WO2012/172411
PCT Pub. Date: Dec. 20, 2012

(65) Prior Publication Data
US 2014/0120171 A1    May 1, 2014

Related U.S. Application Data

(63) Continuation-in-part of application No. 13/161,101, filed on Jun. 15, 2011, now Pat. No. 8,895,074.

(30) Foreign Application Priority Data

Sep. 2, 2011 (EP) ...................... 11179821

(51) Int. Cl.
| | | |
|---|---|---|
| *A61K 35/612* | (2015.01) | |
| *A61K 9/00* | (2006.01) | |
| *A61K 9/113* | (2006.01) | |
| *A61K 35/60* | (2006.01) | |
| *A61K 31/683* | (2006.01) | |
| *A61K 45/06* | (2006.01) | |
| *A61K 9/107* | (2006.01) | |
| *A61K 31/23* | (2006.01) | |
| *A61K 31/6615* | (2006.01) | |
| *A61K 31/407* | (2006.01) | |
| *A61K 31/7036* | (2006.01) | |
| *A61K 47/46* | (2006.01) | |

(52) U.S. Cl.
CPC .......... *A61K 35/612* (2013.01); *A61K 9/0019* (2013.01); *A61K 9/107* (2013.01); *A61K 31/23* (2013.01); *A61K 31/407* (2013.01); *A61K 31/6615* (2013.01); *A61K 31/683* (2013.01); *A61K 31/7036* (2013.01); *A61K 45/06* (2013.01); *A61K 47/46* (2013.01)

(58) Field of Classification Search
CPC ........ A61K 35/612; A61K 9/00; A61K 9/113; A61K 35/60
USPC ................................. 424/400, 523
See application file for complete search history.

(56) References Cited

U.S. PATENT DOCUMENTS

| | | | |
|---|---|---|---|
| 5,434,183 A | 7/1995 | Larsson-Backstrom | |
| 6,284,268 B1 | 9/2001 | Mishra et al. | |
| 2006/0078625 A1 | 4/2006 | Rockway | |
| 2008/0274203 A1 | 11/2008 | Bruheim et al. | |
| 2008/0312338 A1 | 12/2008 | Goodale | |
| 2009/0099261 A1 | 4/2009 | Bell et al. | |
| 2010/0062057 A1 | 3/2010 | Berge et al. | |
| 2010/0130619 A1* | 5/2010 | Schwarz et al. ............. 514/690 |
| 2010/0233280 A1 | 9/2010 | Driscoll | |
| 2011/0065673 A1 | 3/2011 | Kanada et al. | |
| 2011/0071090 A1 | 3/2011 | Driscoll | |
| 2011/0305771 A1 | 12/2011 | Sampalis | |

FOREIGN PATENT DOCUMENTS

| | | | |
|---|---|---|---|
| EP | 2 153 736 A1 | 2/2010 |
| JP | 6-508123 A | 9/1994 |
| JP | 8-231391 A | 9/1996 |
| JP | 2001525363 A | 12/2001 |
| JP | 2003535057 A | 11/2003 |
| JP | 2004-534800 A | 11/2004 |
| WO | 2008060163 A1 | 5/2008 |
| WO | 2008117062 A | 10/2008 |
| WO | WO 2008/117062 A1 | 10/2008 |
| WO | 2010029433 A1 | 3/2010 |
| WO | 2010104575 A2 | 9/2010 |
| WO | 2011005113 A1 | 1/2011 |
| WO | 2011051743 A1 | 5/2011 |

OTHER PUBLICATIONS

Carlson et al. Urinary Adenosine Excretion in Patients Receiving Amphotericin B; Surgery, vol. 121, No. 2 (1997) pp. 190-193.*
Karth et al. Role of Amiodarone on the Systemic Inflammatory Response Induced by Cardiac Surgery: Proinflammatory Actions; Canadian Journal of Anesthesiology, vol. 54, No. 4 (2007) pp. 262-268.*
International Search Report (PCT/ISA/210) dated Jul. 26, 2012, by the European Patent Office as the International Searching Authority for International Application No. PCT/IB2012/001156.
Goldfarb et al., "Protein-free phospholipid emulsion treatment improved cardiopulmonary function and survival in porcine sepsis", Am J Physiol Regul Integr Comp Physiol., 2003, vol. 284, No. 2, pp. R550-R557.
Cave et al., "Intravenous Lipid Emulsion as Antidote Beyond Local Anesthetic Toxicity: A Systematic Review", Acad Emerg Med, 2009, vol. 16, No. 9, pp. 815-824.
Japanese Office Action issued in corresponding Japanese Patent Application No. 2014-515299 dated Aug. 5, 2015, and translation thereof.

(Continued)

*Primary Examiner* — Scott Long
*Assistant Examiner* — Paul C Martin
(74) *Attorney, Agent, or Firm* — Buchanan Ingersoll & Rooney PC

(57) ABSTRACT

A method of parenterally administering a composition, the method including parenterally administering to a person a composition including krill oil in an oil-in-water emulsion. A parenterally applicable pharmaceutical composition, including an oil-in-water emulsion including a phospholipid obtained from a marine crustacean.

46 Claims, No Drawings

(56) References Cited

OTHER PUBLICATIONS

Office Action (Notification of the Second Office Action) dated Feb. 23, 2016, by the Chinese Patent Office in corresponding Chinese Patent Application No. 201280028987.7 and a partial English Translation of the Office Action. (11 pages).
Russian Office Action dated Aug. 17, 2016 in Application No. 2014101067/15(001394) (with English translation).
Alternative Medicine: Maintaining Brain Health with Kriella, Apr. 6, 2011 (on-line) (found on Apr. 13, 2016), http://astiro-med.blogspot.ru/2011/04/1.html (with English machine translation).
A.P. Vlasov et al., "About effect of antioxidants on endotoxicosis expression at experimental peritonitis," Experimental and Clinical Pharmacology, 2000, No. 6, pp. 58-61, abstract (on-line) (found on Apr. 8, 2016), www.fesmu.ru/elib/Article.aspx?id=51783 (with English machine translation), abstract only.
S.F. Bagnenko et al., "Pharmacological correction of metabolic disorders in patients with widespread peritonitis," Emergency Medical Care, 2008, No. 2, pp. 44-48 (abstract (on-line) (found on Apr. 8, 2016), www.fesmu.ru/elib/Article.aspx?id=186457 (with English machine translation), abstract only.
Office Action (Notice of Office Action) dated Aug. 30, 2017, by the Korean Patent Office in corresponding Korean Patent Application No. 10-2014-7001111, and an English Translation of the Office Action. (13 pages).
Canadian Office Action dated Mar. 20, 2018, issued by the Canadian Intellectual Property Office in corresponding Canadian Patent Application No. 2,838,312 (3 pages).

\* cited by examiner

THERAPEUTIC APPLICATION OF PARENTERAL KRILL OIL

CROSS-REFERENCE TO RELATED APPLICATIONS

The present application is a national stage filing under 35 U.S.C. 371 of International Application No. PCT/IB2012/001156 filed Jun. 13, 2012, which in turn is a continuation-in-part of U.S. application Ser. No. 13/161,101 filed on Jun. 15, 2011, now U.S. Pat. No. 8,895,074, and claims the benefit of priority of European Patent Application No. 11179821.1 filed on Sep. 2, 2011.

BACKGROUND

Krill oil is a unique marine oil containing omega-3 or n-3 fatty acids (FAs), wherein the bioactive eicosapentaenoic acid (EPA) and docosahexaenoic acid (DHA) are present (i.e., comprising up to 35%$_{w/w}$ of the FA profile) mainly in phospholipids or PLs (up to 95%$_{w/w}$), and containing up to 60% PLs and up to 45% triglycerides in the oil.[1] In contrast, current sources of n3-FAs in commercial parenteral or injectable lipid emulsions consist of approximately 30 to 60%$_{w/w}$ concentration, but are nearly entirely contained in fish oil triglycerides (TG). Of note, the European Pharmacopeia (Pharm Eur) has two official monographs for n3-FAs derived from fish oil triglycerides. The first monograph was adopted in 1999 and includes the following title, monograph number and specifications:
1. Omega-3 Acid Triglycerides, Pharm Eur Monograph 1352
   (Omega-3 acidorum triglyceride)
   Content:
      Sum of the contents of the omega-3 acids EPA and DHA, expressed as triglycerides: minimum 45.0 percent; total omega-3 acids, expressed as triglycerides: minimum 60.0 percent.

In 2005, a second Pharm Eur monograph was adopted and includes the following title, monograph number and specifications:
2. Fish Oil, Rich in Omega-3 Acids, Pharm Eur Monograph 1912
   (*Piscis oleum* omega-3 acidis abundans)
   Content:
      EPA, expressed as triglycerides: minimum 13.0 percent,
      DHA, expressed as triglycerides: minimum: 9.0 percent,
      total omega-3 acids, expressed as triglycerides: minimum 28.0 percent.

Of the two monographs, only Pharm Eur Monograph 1352 is specifically indicated for parenteral use.[2] However, depending upon the manufacturer, two commercially available parenteral emulsions employ the pharmacopeial standards of either Monograph 1352 or 1912, i.e., one brand of fish oil-containing injectable emulsion contains approximately one-half the concentration of the bioactive omega-3 fatty acids, EPA and DHA vs. another brand of fish oil-containing emulsion, and hence they are not bioequivalent.[3] Ideally, it may be beneficial to employ the specifications of Pharm Eur Monograph 1352, a greatly purified fish oil triglyceride source of n3-FAs, especially when administered by the intravenous route of administration.

Omega-3 fatty acids are classified as highly polyunsaturated fatty acids (PUFA), containing multiple double bonds that are extremely susceptible to oxidative degradation. Unsaturated fatty acids have specific nomenclature involving 3 general terms: 1) number of carbons; 2) number of double bonds; and, 3) the carbon containing the first double bond. There are 3 main families of unsaturated fatty acids important in human metabolism and they include the omega-3's (e.g., EPA containing 20 carbons, 5 double bonds beginning on the $3^{rd}$ carbon from the methyl end of the hydrocarbon chain, denoted as 20:5n3); the omega-6's (e.g., arachidonic acid, or AA, containing 20 carbons, 4 double bonds beginning on the $6^{th}$ carbon, denoted as 20:4n6); and finally, the omega-9's (e.g., oleic acid containing 18 carbons, 1 double bond beginning on the $9^{th}$ carbon, denoted as 18:1n9). They are classified as highly polyunsaturated, polyunsaturated, and monounsaturated fatty acids, respectively. Oxidation of highly PUFAs, such as EPA (20:5n3) and DHA (22:6n3), not only degrades their important clinical bioactivities (such as therapeutic decreases in: inflammation, oxidative stress, immunosuppression and ischemia), but also produces volatile degradation products known as reactive oxygen species, that may have clinically relevant and harmful side effects to vital organs (e.g., heart, brain, lungs, liver and kidneys), especially in critically ill patients during acute metabolic stress (i.e., the systemic inflammatory response syndrome). Therefore, minimizing the oxidation of vegetable- or marine-based polyunsaturated fatty acids in injectable lipid emulsions is desirable. This can be achieved based on the location of the polyunsaturated fatty acid on the glyceride backbone, with position-2 being most preferable in this regard (as well as with respect to bioavailability). Alternatively, antioxidants, such as alpha tocopherol, are either naturally present in small amounts (e.g., alpha-tocopherol in soybean oil, ~20 mg/L) or are added to the lipid injectable emulsion formulation in amounts approximating 200 mg/L. Alpha-tocopherol is an example of a parenteral antioxidant that protects these bioactive fatty acids from chemical breakdown and subsequent potential clinical harm, and it is recognized as a suitable parenteral pharmaceutical adjuvant by both the European and the United States Pharmacopeias (USP). On the other hand, in addition to its high PL contents, krill oil possesses another unique attribute, in that it contains the naturally occurring antioxidant, astaxanthin, but in amounts 10× to 100× higher than the antioxidants naturally found in commonly used polyunsaturated triglyceride oil-in-water parenteral emulsions.[1] Astaxanthin is not approved for use in humans as a parenteral surfactant.

Despite this benefit, the uniquely high PL content of krill oil (e.g., in its current composition') may render it unsuitable as a major source of n-3 FAs in lipid injectable emulsions. Current parenteral dispersions contain egg phospholipids as a surfactant to stabilize various triglyceride oil-in-water (o/w) emulsions. Like egg phospholipids, phosphatidyl choline is a major phosphatide in krill oil phospholipids.[4] The proportion of phospholipids to triglycerides (PL:TG ratio) in injectable lipid emulsion formulations should be no greater than 0.06. For example, a standard 20% soybean oil-in-water injectable lipid emulsion contains 12 g/L of PL and 200 g/L of triglycerides. Higher PL:TG ratios (i.e., 0.12, e.g., 10% oil-in-water emulsions with 12 g/L of egg PL) have been shown to interfere with lipoprotein lipase and impair plasma clearance of infused triglycerides (i.e., hypertriglyceridemia) in acutely ill infants, and in adults at high infusion rates.[5] Therefore, using krill oil in its present form as the principal lipid source in injectable emulsions does not seem to be clinically acceptable.

Another high concentration parenteral phospholipid-based injectable emulsion (92.5% phosphatidyl choline/7.5% triglyceride) has been given in an attempt to neutralize the clinical sequelae from bacterial endotoxin.[6] Although some benefits were observed, the primary study endpoint, a non-parametric "clinical scoring system" based on various symptoms (chills, headaches, myalgias, nausea and headaches), was applied[6] and analyzed by parametric statistical methods (i.e., a 2-tailed t-test). However, this significant design flaw negated the purported benefits of the study. A follow-up randomized clinical trial involving 235 medical centers worldwide showed no significant benefit on 28-day all-cause mortality, nor was there a reduction in the onset of new organ failure.[7] Moreover, the high-dose arm of the study had to be stopped due to an increase in life-threatening adverse events. It is possible, as with effective parenteral surfactants, that a mixture of phosphatides is more efficacious as a pharmaceutical aid, and that a similar composition may be needed for clinical safety and efficacy in this patient population.

SUMMARY

According to an exemplary embodiment, a method of parenterally administering a composition is provided, the method comprising parenterally administering to a person a composition comprising krill oil in an oil-in-water emulsion.

According to another exemplary embodiment, a parenterally applicable pharmaceutical composition is provided, comprising an oil-in-water emulsion comprising a phospholipid obtained from a marine crustacean.

DETAILED DESCRIPTION

According to an exemplary aspect, provided is a composition having an omega-3 fatty acid-containing phospholipid obtained from, for example, a marine crustacean such as krill. The use of exemplary compositions in various applications, for example, as a surfactant, as a therapy for endotoxicosis in sepsis, and/or as an antidote for lipophilic drugs, can result in improvements in the safety and efficacy over existing therapies. Such composition can be administered parenterally. According to an exemplary aspect, therapeutic indications of a marine oil obtained from a crustacean, for example, krill oil, in parenteral dosage forms for treatment of several clinical conditions are provided.

The composition can contain an oil obtained from a marine crustacean such as, for example, krill (Euphausiacea). As used herein, the term "krill oil" can include an oil directly obtained from krill, an oil which is derived from a krill source and which has been further modified/processed, and combinations thereof.

The krill oil contains phospholipids to which omega-3 fatty acids are attached. For example, the krill oil can contain omega-3 fatty acid-containing phospholipids in an amount of about 20 to about 60%, for example, from about 30 to about 50%, based on the weight of the krill oil. In an exemplary embodiment, the krill oil can contain omega-3 fatty acid-containing triglycerides in an amount of less than about 30%, for example, less than about 5%, based on the weight of the krill oil. In an exemplary embodiment, the krill oil can be substantially free of omega-3 fatty acid-containing triglycerides. For example, both phospholipids (PLs) and triglycerides (TGs) possess a 3-carbon backbone (triacylglycerol) where certain functional groups attach to each of the carbons, with positions-1, -2, and -3 noted as sn1, sn2 and sn3, respectively. The sn1 and sn2 positions in both PLs and TGs can contain long-chain fatty acids, such as 18-carbon compounds (e.g., linoleic, alpha-linolenic, oleic and stearic acids) and/or very-long chain fatty acids containing 20 or more carbons (e.g., arachidonic, eicospentaenoic, docsapentaenoic and docosahexaenoic acids). In TGs, the sn3 position is also occupied by the above long-chain fatty acids, and as such these compounds are known as "neutral fat", whereas in PLs the sn3 position is occupied by phosphoric acid bound to an alcohol such as choline, ethanolamine, serine, inositol, etc., that significantly alters the molecule, conferring to it both hydrophilic and hydrophobic properties, known as an amphiphilic compound. As part of the structural make-up of biological membranes, and possessing amphiphilic properties, PLs serve a vital role in many metabolic processes.

In an exemplary embodiment, a pre-determined amount of the omega-3 fatty acid-containing phospholipids contain omega-3 fatty acids attached to the first and second positions of the phospholipid, but not the third position of the phospholipid. That is, a predetermined amount of the omega-3 fatty acid-containing phospholipids can contain an omega-3 fatty acid in the second position (i.e., the middle position) of the phospholipid. For example, the omega-3 fatty acid-containing phospholipids containing omega-3 fatty acids attached to the first and second positions of the phospholipid, but not the third position of the phospholipid, can be present in an amount of about 70% to about 80%, for example, from about 80% to about 95%, based on the total weight of the omega-3 fatty acid-containing phospholipids.

In an exemplary embodiment, the marine crustacean or krill oil can be distinguishable from fish oils at least based on (1) the phospholipid contents, (2) the content of omega-3 fatty acid-containing phospholipids, (3) the content of omega-3 fatty acid-containing triglycerides, and/or (4) the content of the omega-3 fatty acid-containing phospholipids which contain omega-3 fatty acids attached to the first and second positions of the phospholipid, but not the third position of the phospholipid. For example, the marine crustacean or krill oil can contain a higher concentration of omega-3 fatty acid-containing phospholipids, a lower concentration of omega-3 fatty acid-containing triglycerides, and/or a higher content of the omega-3 fatty acid-containing phospholipids which contain omega-3 fatty acids attached to the first and second positions of the phospholipid, but not the third position of the phospholipid.

In a preferred embodiment the composition of the invention comprises a mixture of krill oil and a parenterally applicable oil different from krill oil, preferably fish oil. The weight ratio of fish oil to krill oil in the composition is usually 1:1 to 200:1, preferably 4:1 to 150:1, further preferably 5: to 100:1, more preferably 8:1 to 50:1, especially 9:1 to 25:1.

Fish oil used in the present invention can represent oils from a variety of fatty fish families, such as from the following species: Engraulidae (e.g., anchovies), Carangidae (e.g. mackerel), Clupeidae (e.g. herring), Osmeridae (e.g. smelt), Salmonidae (e.g. salmon) and Scombridge (tuna).

The amount of the krill oil in the composition can depend, for example, on the specific application of the composition. For example, the krill oil can be present in an amount of from about 1% to about 20%, for example, from about 5% to about 10%, based on the total weight of the composition.

The ratio of oil to water in the oil-and-water emulsion can depend, for example, on the specific application of the composition. For example, the weight ratio of oil to water in the composition can range from about 1:99 to about 20:80, for example, from about 5:95 to about 10:90.

The composition can contain additional components, and the presence and amounts of the additional components can depend, for example, on the specific application of the composition. Exemplary examples of emulsion compositions are set forth in Table 1. For example, the composition can include a fish oil, MCT oil, and/or egg phospholipids. For example, the composition can include a total fish oil content of from about 0% to about 18%, for example, from about 5% to about 10%, based on the weight of the composition. The fish oil can include n3-FA-containing triglycerides. For example, the composition can include a total MCT oil content of from about 0% to about 10%, for example, from about 4% to about 8%, based on the weight of the composition. For example, the composition can include a total egg phospholipid content of from about 0% to about 1.8%, for example, from about 0.6% to about 1.2%, based on the weight of the composition. For example, the composition may contain astaxanthin of from about 0.0012% to about 0.02%, for example, from about 0.04% to 0.25%, based on the weight of the composition. Exemplary fish oils, MCT oils and egg phospholipids and contents thereof are disclosed in U.S. application Ser. No. 12/382,196 filed on Mar. 11, 2009, and International Application No. PCT/US2010/000723 filed Mar. 11, 2010, the entire contents of which are incorporated by reference herein.

For example, the krill oil can be used as an additive in an omega-3 enriched fish oil-in-water parenteral nutrition emulsion. The krill oil can be used in conjunction with the compositions and/or methods disclosed in International Application No. PCT/US2010/000723 filed on Mar. 11, 2010; U.S. application Ser. No. 12/382,196 filed on Mar. 11, 2009; and/or U.S. application Ser. No. 12/923,257 filed on Sep. 10, 2010, the entire contents of which are incorporated by reference herein.

The krill oil can be subjected to various processing steps, and the specific processing steps employed can depend on, for example, the desired characteristics of the oil. For example, modifications or purifying steps are possible, and may be desirable in order to optimize the clinical utility of this unique source of n3-FAs. These changes, for example, may include deliberate alterations in the fatty acid profiles of the krill oil, such as 1) increasing the concentrations of the bioactive n3-FAs, EPA and DHA (e.g., from up to 35% w/w to 45% w/w); 2) changing the distribution of these bioactive omega-3 fatty acid levels in the phospholipids fraction or the triglyceride (TG) fraction of the oil (e.g., ↑PL ↓TG, ↓PL ↑TG, PL=TG); 3) maximizing the probability of locating the n3-FAs in the 2-position of the phospholipids (to optimize incorporation into biological membranes, and enhance stability); 4) reducing the concentration of potentially clinically deleterious saturated fatty acids[8] present (e.g., myristic acid, 14:0 and palmitic acid, 16:0); 5) reducing the concentration of free fatty acids; 6) minimizing the presence of lysophosphatidyl choline; 7) modifying the effective concentrations of astaxanthin, as well as any other pharmaceutical modifications to render the krill oil safe for intravenous administration. Table 2 provides examples of modifications of fatty acids and lipids from current krill oil compositions[1] that might be designed by applying appropriate physical and chemical methods to form specialized compositions in order to achieve certain clinical applications. The examples are in no way meant to be limiting but to illustrate the possibilities recognizing there are numerous permutations and combinations possible. The high concentration of PLs in krill oil is unique among marine oil sources, and the possible modification of the natural source can exploit this aspect, for example, with respect to manipulating the composition to enhance the clinical (likelihood of structuring a stereospecific preponderance for the signaling n3-FAs, i.e., EPA and DHA, in the 2-position of the PLs present) and pharmaceutical (safe and efficacious parenteral marine oil) attributes.

According to an exemplary aspect, a method of parenterally administering a composition is provided, the method comprising parenterally administering to a person a composition containing krill oil in a parenteral oil-in-water emulsion as an alternative surfactant to egg lecithin or in combination with egg lecithin to improve the physical stability of the emulsion (Table 3). Achieving the physical stability of an injectable emulsion is defined as maintaining a homogenous distribution of submicron droplets, and minimizing the population of large-diameter (>1 micrometer) fat globules. During instability, the population of large-diameter fat globules grow (via coalescence or fusion of submicron lipid droplets), increasing the danger (e.g., pulmonary embolism, hypertriglyceridemia, liver dysfunction) from the injectable emulsion upon infusion. PLs can be used to stabilize the injectable lipid emulsion by coating the submicron lipid droplets, thereby imparting an electrostatic charge on each and preventing coalescence.

For example, as mentioned, due to the high PL content of krill oil, and the propensity for excess phospholipids in relation to triglycerides in a given formulation that causes hypertriglyceridemia, there can be concentration limits to the fraction of krill oil that can be present in the oil phase of the parenteral emulsion using current krill oil compositions.[1] As a starting point, we know that the ideal PL:TG ratio is 0.06, so, for example, in a $20\%_{w/v}$ oil-in-water emulsion, 12 g of PL/1000 mL meets this ratio. If we assume that one type of krill oil contains approximately 30% PL, and that it has equivalent surfactant properties as conventional egg PLs, then the total krill oil content in a formulation can be adjusted accordingly as shown in Table 3. Thus, in this example, for every 1 g of krill oil, there is 0.3 g of PL present, so therefore up to 40 g can be included in an injectable emulsion, assuming that no additional PL, such as egg phospholipids, are added. For this to occur, the efficacy of krill oil as an equivalent surfactant (i.e., from a pharmaceutical and safety perspective) can be established against the standard parenteral surfactant, egg phospholipids (see below). In the present case, it is assumed that 40 g of krill oil provides equivalent surfactant properties as 12 g of egg phospholipids.

With this presumption, the following are possible formulations employing krill oil as part of a lipid injectable emulsion (International Application No. PCT/US2010/000723), as shown in Table 4 to illustrate some possibilities. If krill oil can be shown to exhibit equivalent behavior as a surfactant in the form of egg phospholipids, then it can replace the latter altogether, or alternatively, it may be used to supplement a portion of the conventional emulsifier. Again, as in the above example, a number of surfactant combinations are possible to optimize the stability of the emulsion system. Several additional examples are shown in Table 5 to exemplify this application using a 20% w/v oil-in-water emulsion (International Application No. PCT/US2010/000723), with 12 g/L of phospholipids using a higher PL-containing krill oil, but these examples are not meant in any way to be inclusive of the possible combinations, but merely to illustrate the concepts in this application. The efficacy of krill oil as a surfactant will be tested against egg phospholipids, since we know that it is a mixture of PLs that provide for the best surfactant. Of course, purification of the krill to remove the triglyceride fraction (i.e., 100% phospholipids) may be particularly desirable for intravenous administration, in which case the amounts of krill oil for surfactant purposes may be equal (by weight) to egg phospholipids. It can also be recognized that purifying krill oil may remove trace, but important, amounts of surfactants which may alter surfactant activity much in the same way that purified egg lecithin, i.e., purified emulsifiers (phosphatidyl choline) have been shown to be inferior to non-purified lecithin. Also, purifying fish may also remove seemingly undesirable, but possibly essential, fatty acids found in small amounts.

At present, reduced stability has been observed during stress testing of marine oil-containing injectable emulsions stabilized by egg phospholipids, compared to plant oil-containing injectable emulsions as depicted in Table 6. A marine oil-based PL-surfactant, such as krill oil, may improve the physical stability of very long-chain triglycerides such as the 20-carbon EPA and 22-carbon DHA, recognizing that the longer the hydrocarbon chain length, the greater the stress (i.e., interfacial tension) between the aqueous and oil phases of the emulsion, and consequently the greater the stress upon the surfactant to maintain physical stability.[9] Krill oil PLs may uniquely exhibit greater stability for these marine oil-based very long-chain triglycerides compared to conventional egg phospholipids emulsifiers when used for conventional 18-carbon long-chain triglycerides from plant sources such as soybean or olive oil. Thus, use of krill oil as a primary or co-surfactant in various high concentration fish oil-in-water parenteral emulsions may significantly improve the physical stability of these very long-chain triglyceride dispersions.

According to another exemplary aspect, a method of parenterally administering a composition is provided, the method comprising parenterally administering to a person a composition containing krill oil in a parenteral oil-in-water emulsion that contains protective concentrations of the naturally-occurring anti-oxidant, astaxanthin, against chemical breakdown or oxidation of the unsaturated n3-FAs present. As described earlier, oxidation of the polyunsaturated n3-FAs leads to the formation of reactive oxygen species that may be harmful upon intravenous administration. Thus, a specific omega-3 rich oil-in-water emulsion needs protection against chemical breakdown. Astaxanthin, found in krill oil, may provide unique protection against the oxidation of the omega-3 fatty acids similar to the presence of alpha-tocopherol in soybean oil that protects against oxidation of the omega-6 fatty acids. As such, just as marine-based PLs found in krill oil contain a high concentration of n3-FAs which may uniquely enhance the physical stability of the emulsion, so too may the presence of astaxanthin in krill oil uniquely enhance the chemical stability of the oil-in-water emulsion. Like the exemplary aspects of krill oil as a primary surfactant, or co-surfactant with egg phospholipids, it might be that astaxanthin can be the primary antioxidant, or co-antioxidant with alpha-tocopherol.

According to another exemplary aspect, a method of parenterally administering a composition is provided, the method comprising parenterally administering to a person a composition containing krill oil in a parenteral oil-in-water emulsion as a pharmaceutical drug vehicle to help solubilize highly lipophilic drugs in sufficient concentrations so as to be a therapeutically feasible injectable dosage form. Water-insoluble drugs, such as propofol, diazepam, and clevidipine, are but a few examples of current drugs that might benefit from krill oil containing high PL levels. What PL level is applied for a given formulation will vary with the drug, and may in fact be tailored to a specific drug or pro-drug, as the case may be.

In a further exemplary aspect of the invention the drug is selected from the group consisting of an amphotericin, quinolone, antineoplastic agent, amiodarone, loop diuretic, azathioprine, cyclosporine, tacrolimus, indomethacin, ketorolac and a combination thereof.

In a further exemplary aspect of the invention the drug is selected from the group consisting of
a) Antibiotics, preferably selected from the group consisting of aminoglycosides, amphotericin, chloramphenicol, ketoconazole, macrolides, quinolones and tetracyclines,
b) Antineoplastic Agents, preferably selected from the group consisting of alkylating agents, antimetabolites, and antimitotics platinum coordination complexes,
c) Anti-Parkinson Agents, preferably selected from the group consisting of levodopa, pramipexole, ropinirole, rotigotine and bromocriptine,
d) Cardiovascular Agents, preferably selected from the group consisting of adenosine, amiodarone, angiotensin converting enzyme (ACE) inhibitors and flecainide,
e) Diuretics, preferably selected from the group consisting of loop diuretics, potassium-sparing diuretics and thiazides,
f) Immunosuppressive Agents, preferably selected from the group consisting of Azathioprine, Cyclosporine, Mycophenolate and Tacrolimus,
g) Psychotropics, preferably selected from the group consisting of haloperidol, monoamine oxidase inhibitors, phenothiazines, serotonin reuptake inhibitors and thioxanthines,
h) Non-Steroidal Anti-Inflammatory Drugs (NSAIDs), preferably selected from the group consisting of acetaminophen, aspirin, ibuprofen, indomethacin and ketorolac; and
i) Pharmaceutical acceptable salts and derivatives of the drugs a) to h).

According to another exemplary aspect, a method of parenterally administering a composition is provided, the method comprising parenterally administering to a person a composition containing krill oil in a parenteral oil-in-water emulsion as a pharmaceutical drug vehicle to help solubilize highly lipophilic drugs in sufficient concentrations in the oil phase, along with a water-soluble salt of said drug in the aqueous phase, so as to be a therapeutically feasible injectable dosage form. In this aspect, the drug may exist as a free acid or base, but may also be present in the same dosage form as a water-soluble salt. For example, the drug ketorolac is highly water insoluble as the free acid, but also exists as the water-soluble tromethamine salt and as such a commercial product currently exists in an aqueous injection at 30 mg/mL. The drug may be better tolerated (e.g., reduced risk of peripheral vein thrombophlebitis) if a portion of the drug is divided between the aqueous and nonaqueous phases of the emulsion. For example, in a conventional oil-in-water emulsion, the oil phase is the internal, or dispersed, phase, where the free acid would reside, and the external, or aqueous, phase would contain the corresponding water-soluble salt. How much it resides in each phase will depend upon the most desirable location with the least side effects. At present, there are cases where the lipophilic drug is intended to reside in the dispersed phase, but some free form of the drug in low concentrations is evitably present in the aqueous phase, where it has caused phlebitis.

For example, propofol dispersed in a long-chain triglyceride (LCT) source, such as soybean oil-in-water emulsion has a higher phlebitis rate than a similar product, but where the lipid phase is now a 1:1 mixture of long-chain and medium-chain triglycerides (MCTs).[10] The improvement in phlebitis symptoms in the latter formulation appears to be related to a reduced aqueous concentration of free propofol, presumably due to enhanced incorporation of the free drug into both lipid fractions, while minimizing the concentration of propofol in the aqueous phase. Therefore, the exemplary aspect described herein is the unique and deliberate use of one or both phases of the emulsion to achieve the optimal dosage form that can safely and efficaciously deliver the active pharmaceutical ingredient (U.S. application Ser. No. 12/923,257).

According to another exemplary aspect, a method of parenterally administering a composition is provided, the method comprising parenterally administering to a person a composition containing krill oil in a parenteral oil-in-water emulsion as a therapeutic drug vehicle providing n3 fatty acids to mitigate adverse drug effects to vital organs (brain, heart, lungs, liver and kidney) involving inflammation, oxidative stress, immune modulation and/or ischemic events. The use of krill oil alone or in combination with fish oil triglycerides can be included in a parenteral dosage form for drugs known to cause damage to vital organs whose mechanism of injury involves inflammation, oxidative stress, ischemia and/or immune dysfunction as previously described in U.S. application Ser. No. 12/923,257.

According to another exemplary aspect, a method of parenterally administering a composition is provided, the method comprising parenterally administering to a person a composition containing krill oil in a parenteral oil-in-water emulsion as a safer treatment for endotoxicosis during severe sepsis. Endotoxin, and more specifically lipoploysaccharide (LPS), is present in the outermost membrane of bacterial cell walls, and is capable of eliciting a profound systemic inflammatory response in patients with blood stream infections. As the body responds to the presence of microorganisms in the blood stream via normal immune responses, e.g., phagocytosis, the bacterial cell wall is broken down and the Lipid A component of the outer cell wall remnant is released into the systemic circulation, where it stimulates the immune response and provokes systemic inflammation through various endogenous mediators involving cytokines, e.g., interleukin-1 (IL-1), tumor necrosis factor (TNF), eicosanoids (prostaglandins, thromboxanes, leukotrienes), catecholamines and hormones. In the infected patient, LPS can produce "systemic inflammatory response syndrome", or SIRS, that is characterized by dysregulations in body temperature, white blood cell counts, glucose homeostasis, coagulation, and vital organs functions (brain, heart, lungs, liver and kidneys). In a classical study of patient outcomes from SIRS, the mortality rate rose from 7% for non-infectious causes to as high as 46% from infectious causes.[11] Treatment for severe sepsis or septic shock has been directed at neutralizing the effects of endotoxin with antibodies or with agents that bind the endotoxin in the blood stream, rendering it inactive with lipoproteins or phospholipids. To date, these approaches have not been effective and have been associated with significant safety issues.

A further exemplary embodiment of the present invention is a method for parenterally administering a composition, the method comprising parenterally administering to a person a composition comprising a phopholipid obtained from krill (Euphausiacea) in an oil-in-water emulsion, wherein after administration said phospholipid binds with an endotoxin.

As described earlier, PLs have been shown to confer a significant survival advantage in animals, but they ultimately failed in clinical trials. The phospholipid agent used in these trials contained 92.5% soy phosphatidyl choline and 7.5% soy triglycerides.[6] As the PL concentrations in krill oil are present in amounts up to 60% w/w, with phosphatidyl choline as a major phosphatide constituent, krill oil may be an effective alternative to previous attempts in treating endotoxicosis using higher concentration PL formulations derived from vegetable sources. For example, approximately 50% of the fatty acid profile of soybean oil triglycerides consists of the pro-inflammatory omega-6 fatty acid (n6-FA) linoleic acid (18:2n6), which may adversely accentuate the inflammatory response during SIRS and sepsis. Moreover, intravenous fat emulsions stabilized by soy-based phosphatides have been associated with severely adverse effects in laboratory animals, whereas egg phospholipids were shown to be devoid of these effects.[12] Of six animals receiving these emulsions, 2 died within 48 hours of starting the infusion, and the remaining four developed "significant hyperpyrexia" following infusion, along with an approximate 50% reduction in food and water intake.[12] At present, egg phospholipids are nearly universally used in most nutritional and drug-containing injectable lipid emulsions. In contrast, given the unique composition of krill oil, which contains the less anti-inflammatory n3-FAs, contains a lower PL concentration, and can be stabilized with either egg PLs alone, krill oil PLs alone, or a combination of the two, the use of krill oil may avert previous clinical problems. These changes may yield a safer and more effective treatment option for endotoxin therapy in acutely ill patients with sepsis.

According to another exemplary aspect, a method of parenterally administering a composition is provided, the method comprising parenterally administering to a person a composition containing krill oil in a parenteral oil-in-water emulsion as an antidote to bind highly lipophilic drugs that may cause systemic toxicity.[13] Lipid emulsions have been used in the treatment of toxicity arising from lipophilic drugs, such as local anesthetics (e.g., bupivicaine), tricyclic antidepressants (e.g., amitryptyline) and cardiovascular agents including calcium channel blockers (e.g., verapamil) and antiarrhythmics (e.g., amiodarone), and in organophosphate poisoning from insecticides, etc. Presumably, the lipid emulsion vehicle sequesters the drug from the blood stream, thereby reducing the toxic manifestation caused by the free drug in the circulation. Unfortunately, there are limits to the delivery rate and volume of conventional long-chain triglyceride-based injectable emulsions that can be safely administered. Currently, a soybean oil-in-water emulsion is most widely used, but contains high amounts of pro-inflammatory n6-FAs (i.e., linoleic acid). When administered by rapid intravenous administration, they can produce acute, and clinically significant pulmonary gas diffusion abnormalities,[5] that would be particularly undesirable in the unconscious patient with drug overdose, especially in the absence of mechanical ventilation. Moreover, the maximum metabolic capacity of the human body to clear long-chain triglycerides is approximately 0.11 g/kg/hour,[5] and thus, complications to other vital organs (e.g., liver), as well as coagulation disorders from fat overload syndrome, can occur. In a test of the safety of high volume lipid infusion in laboratory animals, doses of 20% soybean oil-in-water emulsion ranging from 20 to 80 mL/kg were administered over 30 minutes, with lethal doses occurring at 60 and 80 mL/kg, but all doses were much higher than those used in the clinical setting as an antidote, of approximately 5 mL/kg.[14] Even at this lower human dose, current use of this injectable emulsions as antidote therapy clearly exceeds the metabolic capacity in humans in a 30 minute infusion (i.e., by >1 log higher). Use of a specially designed injectable emulsion containing only krill oil, or krill oil possibly in combination with a small amount of triglycerides, may be a safer and more effective antidote for lipophilic drug toxicities. This is because PLs are most likely responsible for binding and inactivating lipophilic drugs that cause toxicity, just as the same PLs are components for neutralizing the adverse sequelae of endotoxin. Hence, the safe, as well as effective delivery of PL infusions is most desirable and krill oil injectable emulsions may be uniquely beneficial in this regard.

A further exemplary embodiment of the present invention is a method for parenterally administering a composition, the method comprising parenterally administering to a person a composition comprising a phopholipid obtained from krill (Euphausiacea) in an oil-in-water emulsion, wherein after administration said phospholipid binds with a highly lipophilic drug.

According to another exemplary aspect, a method of parenterally administering a composition is provided, the method comprising parenterally administering to a person a composition containing krill oil in a parenteral oil-in-water emulsion as a source of n3-FAs to prevent essential fatty acid deficiency (EFAD). For example, to prevent EFAD in humans, at least 1% of the calories can come from the diet typically as linoleic acid (18:2n6), and approximately 0.5% from alpha-linolenic acid (18:3n3), in order to meet the n6- and n3-fatty acid (FA) requirements, respectively.[15] Thus, for example, in a 40 kg patient receiving a 1000 kcal diet, where soybean oil is the principal fat source (FA profile containing approximately 50% linoleic acid and approximately 10% alpha-linolenic acid), approximately 2 grams would meet n6-FA needs, whereas to meet n6-FA and n3-FA requirements, approximately 5 grams would have to be provided. But unlike common vegetable oil sources used in injectable lipid emulsions, marine oils (e.g., fish oil triglycerides and krill oil phospholipids) contain approximately 0.5% of the total FA profile as the essential n6-FA, arachidonic acid (AA), and approximately 20 to 60% as the essential n3-FAs, EPA and DHA. This is an important point since conventional vegetable oil sources do not contain appreciable amounts of these essential fatty acids (EFAs), but instead contain mainly their precursors that need to be metabolized enzymatically via several desaturation and elongation steps to form the 20- and 22-carbon EFAs from their 18-carbon sources. Thus, a much reduced quantity of the essential fatty acids is necessary, since the conversion to these bioactive end products is not 100% efficient, which is especially true for the formation of EPA and DHA from alpha-linolenic acid (18:3n3). Moreover, a recent review of the experience of Children's Hospital in Boston in treating over 90 infants with parenteral nutrition-related liver disease or PNALD, providing a 100% fish oil emulsion as monotherapy at 1 g/kg/day, has shown to be "safe and efficacious in reversing PNALD and normalizing EFAD status.[16] Of note, the fish oil injectable emulsion that was used contained between 0.1 to 0.4% AA (20:4n6), so it appears that, at least in the case of infants, a very small dose of krill oil could be used to prevent EFAD, and in amounts that do not interfere with the plasma clearance of infused triglycerides. More recently, the same group recently published its findings for a unique cohort of 10 children receiving parenteral nutrition with fish oil as the sole source of fat calories for a median duration of 14 weeks without evidence of EFAD.[17] It is possible that similarly low levels of AA would be sufficient in adults, but it has not yet been tested in this population. Thus, small amounts of krill oil in a parenteral emulsion formulation could prevent EFAD. Nonetheless, the krill oil composition could be modified to contain higher amounts of AA in tailoring the composition to this indication.

A further embodiment of the present invention is a parenterally applicable pharmaceutical composition, comprising an oil-in-water emulsion comprising a phospholipid obtained from a marine crustacean. Preferably, the marine crustacean is krill (Euphausiacea).

According to further aspect of the invention the composition may further comprise a drug. Suitable drugs are described in conjunction with the method of the invention and are described in more detail hereinafter.

The phospholipid obtained from a marine crustacean is preferably present in an amount effective to solubilize the drug. It has been found that phospholipids obtained from krill are highly effective solubilizing agents for lipophilic drugs. Above all the phospholipids are excellent emulsifier for oil in water emulsions, in particular fish oil in water emulsions.

The compositions of the invention are also suitable for use in the treatment of endotoxicosis during sepsis.

It has been found that the phospholipids (phospholipids obtained from krill, in particular from krill oil) have specific surface active, sequestering, and/or binding properties that includes:

a) Long-term and/or more efficient stabilization of very long-chain triglycerides (20-carbon EPA and 22-carbon DHA) vs. the typical 18-carbon fatty acids such as alpha linolenic acid, as found in conventional parenteral oil-in-water emulsions.

b) Acute life-saving therapy to sequester and neutralize the adverse effects of lipopolysaccharides derived from the cell wall fragments of bacteria in the bloodstream of critically ill patients suffering from sepsis and the systemic inflammatory response syndrome.

c) Acute life-saving therapy to bind and neutralize the toxicity of highly lipophilic drug overdoses where conventional antidotes are least effective.

Further, the composition of the invention is suitable for mitigating adverse drug effects to vital organs involving inflammation, oxidative stress, immune modulation and/or ischemic events.

According to a further aspect of the invention the composition is suitable for use in the treatment of a person having toxic blood levels of highly lipophilic drugs.

In a preferred embodiment the composition comprises the phopholipid obtained from krill in an amount ranging from 0.05 g/l to 100 g/l, preferably 0.1 to 50 g/l, more preferably 0.5 to 30 g/l, especially 5 to 20 g/l, based on the total pharmaceutical composition.

As mentioned before the phospholipids obtained from krill are unique since they comprise omega-3-fatty acid moieties. In a preferred aspect of the invention the omega-3 fatty acid-containing phospholipids contain DHA in an amount of about 10 to about 20 wt.-%, based on the total weight of the fatty acid content of the phospholipids.

Further, the omega-3 fatty acid-containing phospholipids may contain EPA in an amount of about 20 to about 40 wt.-%, based on the total weight of the fatty acid content of the phospholipids.

In a preferred embodiment of the composition of the invention the weight ratio of oil to water in the oil-and-water emulsion is from about 1:99 to about 30:70, preferably 10:90 to 20:80.

In a further preferred embodiment the composition is an oil in water emulsion comprising:
a) phospholipid obtained from krill, preferably in an amount ranging from 1 to 100 g/1000 ml, more preferably 5 to 50 g/1000 ml, especially 6 to 20 g/1000 ml,
b) fish oil, preferably an omega-3 fatty acid component, preferably in an amount of 50 to 250 g/1000 ml, more preferably 100 to 200 g/1000 ml c) water, d) optionally mid chain triglycerides, preferably in an amount ranging from 10 to 150 g/1000 ml, more preferably 20 to 100 g/1000 ml; and e) optionally an antioxidant, such as alpha tocopherol or astaxanthin, preferably in an amount ranging from 0.05 g to 1 g/1000 ml, more preferably 0.1 to 0.5 g/1000 ml.

The amounts refer to the total amount of the emulsion. Unless indicated otherwise all parameter and physical value have been determined at 25° C.

According to a preferred embodiment the weight ratio of fish oil to MCT ranges from 1:1 to 9:1.

Preferably the weight ratio of krill phospholipid to the total amount of triglycerides is less than or equal to 0.06.

In a further aspect the pharmaceutical composition for parenteral administration composition comprises an omega-3-fatty acid component selected from the group consisting of omega-3-fatty acid triglycerides and/or omega-3-fatty acid ester, such as omega-3 fatty acid ethyl ester.

It has been found that advantageously the composition and a drug are simultaneously administered. Accordingly, in a preferred aspect the emulsion comprising the phospholipid obtained from krill and a drug are administered simultaneously. By simultaneously administering of the drug and the emulsion it has been found that toxic side effects of the drug can be reduced, in particular if fish oil or omega-3-fatty acid enriched fish oil is present in the emulsion. In a further aspect of the invention the emulsion comprising the phospholipid obtained from krill and the drug are suitable for use in the treatment or prophylaxis of toxic side effects (such as nephrotoxicity) of said drug.

A further aspect is the composition of the invention for use in mitigating toxicity effects of said drug and wherein the toxicity effects are preferably selected from the group selected from oxidative stress, inflammation, adverse immune response, ischemia and damages of vital organs such as kidney, brain, heart, liver and lung, more preferably adverse drug effects selected from the group consisting of oxidative stress, inflammation, immune stimulation, ischemia of at least one vital organ, and a combination thereof.

Preferably the composition comprises omega-3-fatty acid triglycerides and medium chain triglycerides (MCT).

Preferably the emulsion comprises 5 to 69 wt.-% MCT, preferably 10 to 60 wt.-% or 10 to 50 wt.-%, based on the total amount of the oil component in the emulsion.

Further, preferred is an emulsion comprising an oil component and a water component, the oil component comprising fish oil triglycerides in an amount of about 60% to about 90% based on the weight of the oil component; wherein the fish oil triglycerides comprise omega-3 fatty acids in an amount of at least 60%, based on the total weight of the fatty acids of the fish oil triglycerides; wherein the fish oil triglycerides comprise a total amount of EPA and DHA of at least 45%, based on the total weight of the fatty acids of the fish oil triglycerides; and, at least one medium-chain triglyceride, wherein a total amount of the at least one medium-chain triglyceride is from about 10% to about 40% based on the weight of the oil component.

Preferably, the omega-3-fatty acid component comprises eicosapentaenoic acid in an amount of 30 wt.-% or greater, docosahexaenoic acid in an amount of 30 wt.-% or greater, and docosapentaenoic acid in an amount of about 10% or less, based on the weight of the total omega-3 fatty acid content.

The pharmaceutical composition is preferably suitable for use in the treatment by daily parenteral administration of said omega-3 fatty acid in an amount of about 1 to about 300 mg/kg.

In case the composition comprises a drug said drug is usually a material that damages a vital organ when the material is not simultaneously administered with the at least one omega-3 fatty acid.

The drug may be present in an amount of about 0.005% to about 1.5%, based on the weight of the composition.

In general the composition is suitable for use in the treatment by daily parenteral administration of said drug in an amount of about 0.5 to about 50 mg/kg body weight.

According to a specific embodiment the composition comprises an oil in water emulsion comprising omega-3-fatty acid triglycerides and mid chain triglycerides and a drug selected from ketorolac and gentamicin. It has been found that said composition is particularly suitable for use in mitigating the nephrotoxicity of a drug selected from ketorolac and gentamicin.

The drug is preferably a Non-Steroidal Anti-Inflammatory Drug selected from the group consisting of acetaminophen, aspirin, ibuprofen, indomethacin, ketorolac as well as the pharmaceutical acceptable salts and derivatives thereof for use in the treatment or prophylaxis of pain or swelling or redness or fever or inflammation, especially for use in the treatment or prophylaxis of severe acute post-operative pain.

In another aspect the drug is ketorolac or a pharmaceutical acceptable salt of ketorolac, such as ketorolac tromethamine, and the composition is suitable for use in the treatment or prophylaxis of pain or swelling or redness or inflammation, especially for use in the treatment of severe acute post-operative pain.

In particular the composition is for use in the treatment by daily parenteral administration of ketorolac tromethamine in a single dose of more than 60 mg, preferably more than 75 mg; and in multiple doses of more than 120 mg/day, preferably more than 150 mg/day.

In a further aspect the drug is acetaminophen and the composition is for use in the treatment or prophylaxis of pain and/or fever. In this aspect the composition is suitable for use in the treatment of patients weighing ≥50 kg by daily parenteral administration of acetaminophen in a single dose of more than 1000 mg, preferably more than 1250 mg; and in multiple doses of more than 4000 mg/day, preferably more than 5000 mg/day.

In a specific embodiment the composition is for use in the treatment of patients weighing less than 50 kg by daily parenteral administration of acetaminophen in a single dose of more than 15 mg/kg of body weight, preferably more than 18.75 mg/kg; and in multiple doses of more than 75 mg/kg/day, preferably more than 93.75 mg/kg/day.

In a further aspect the drug is indomethacin or a pharmaceutical acceptable salt of indomethacin for use in the treatment for closing a hemodynamically significant patent ductus arteriosus in premature infants weighing between 500 g and 1750 g, preferably when usual medical management is ineffective. In particular said composition is for use in the treatment of premature infants weighing between 500 g to 1750 g by parenteral administration of three intravenous courses at 12 to 24 hour intervals with the first dose of more than 0.2 mg/kg, preferably more than 0.25 mg/kg and a total dose of up to more than between 0.4 mg/kg and 0.7 mg/kg, preferably more than between 0.5 mg/kg and 0.875 mg/kg.

In a further aspect the drug is an aminoglycoside antibiotic selected from the group consisting of amikacin, gentamicin, tobramycin and pharmaceutical acceptable salts thereof for use in the treatment and prophylaxis of infections.

In a further aspect the drug is amikacin or a pharmaceutical acceptable salt of amikacin, such as amikacin sulfate, for use in the treatment and prophylaxis of infections, especially infections with multi-drug-resistant Gram negative bacteria such as *Pseudomonas aeruginosa, Acinetobacter, Enterobacter, Serratia marcescens* and *Providencia stuartii* or for use in the treatment or prophylaxis of non-tubercular mycobacterial infections and tuberculosis.

Preferably the composition of the invention is for use in the treatment by daily parenteral administration of amikacin sulfate in a doses higher than 15 mg/kg body weight, preferably more than 20.25 mg/kg body weight.

In a further aspect the drug is Gentamicin or a pharmaceutical acceptable salt of gentamicin, such as gentamicin sulfate, for use in the treatment or prophylaxis of infections, especially systemic and urinary-tract-infection, life-threatening infections, chest-infections, bacteraemia, septicaemia, severe neonatal infections, more especially infections by *Escherichia coli, Klebsiella* spp., *Proteus* spp., *Pseudomonas aeruginosa, Staphylococci, Enterobacter* spp., *Citrobacter* spp. and *Providencia* spp.

Preferably the composition is for use in the treatment by daily parenteral administration of gentamicin sulfate in a single dose of more than 160 mg/kg body weight, preferably more than 224 mg/kg body weight; and in multiple doses of more than 5 mg/kg body weight/day, preferably more than 7 mg/kg body weight/day.

In a further aspect the drug is Tobramycin or a pharmaceutical acceptable salts of Tobramycin for use in the treatment of infections, especially central nervous system infections including meningitis, septicaemia, and neonatal sepsis or gastro-intestinal infections including peritonitis or urinary tract infections such as pyelonephritis and cystitis or lower respiratory tract infections, including pneumonia, bronchopneumonia and acute bronchitis or skin, bone and soft tissue infections including burns.

Preferably, the composition is for use in the treatment by daily parenteral administration of tobramycin in a single dose higher than 5 mg/kg body weight, preferably more than 6.75 mg/kg body weight; and in multiple doses of more than 20 mg/kg body weight/day, preferably more than 27 mg/kg body weight/day.

In a further aspect the drug is amiodarone or a pharmaceutical acceptable salt amiodarone, such as amiodarone hydrochloride, for use in the treatment or prophylaxis of cardiac arrhythmia or Wolff-Parkinson-White syndrome, especially tachyarrhythmias selected from the group consisting of supraventricular tachycardias, nodal tachycardias, ventricular tachycardias, atrial flutter, atrial fibrillation and ventricular fibrillation.

Preferably, the composition is for use in the treatment by daily parenteral administration of amiodarone hydrochloride in a dose over the first 24 hours of more than 1000 mg, preferably more than 1250 mg; and more than 720 mg as maintenance infusion over 24 hours, preferably more than 900 mg over 24 hours.

In a further aspect the drug is selected from the group consisting of an antineoplastic agents for use in reducing the toxicity to vital organs.

In a further aspect the drug is selected from the group consisting of an antineoplastic agents for use in enhancing the toxicity against tumor cells.

In a further aspect the drug is selected from the group consisting of an antineoplastic agents for use in simultaneously reducing the toxicity of the drug and enhancing its toxicity against tumor cells, preferably for use in the treatment of cancer.

Further, krill phospholipid can be used alone or together with other phospholipids, such as egg phospholipid as emulsifier for an parenterally applicable oil in water emulsion. Especially good results can be achieved by using the krill phospholipid as surfactant or emulsifier for fish oil in water emulsions, especially for omega-3-fatty acid enriched fish oil in water emulsions. Surprisingly the emulsions which are emulsified by the krill phospholipid are physically more stable than emulsions with comparable amounts of egg phospholipids.

Therefore, a further embodiment of the present invention is the use of a krill phospholipid as an emulsifier for an oil in water emulsion, in particular a fish oil in water emulsion.

As mentioned above krill phospholipid or the composition of the invention can be used to bind or neutralize the toxicity of drugs, in particular in critical situations where the drug has been overdosed. Therefore, a further embodiment of the invention is a krill phospholipid or the composition of the invention for use in binding or neutralizing the toxicity of drug overdoses or for use in mitigating adverse drug effects or for use as an antidote for overdosed drugs.

Further, the krill phospholipids can be used in the treatment of endotoxicosis, in particular in sepsis.

Therefore, a further embodiment of the invention is a krill phospholipid or the composition of the invention for use in the treatment of endotoxicosis in sepsis.

According to another exemplary aspect, a method of parenterally administering a composition is provided, the method comprising parenterally administering to a person a composition comprising krill oil in a parenteral oil-in-water emulsion as a daily caloric source of lipids in conjunction with other oils present as shown in Table 1. It is possible that krill oil can be added to current injectable oil-in-water emulsions as a daily caloric source. Due to the limitation that will be likely imposed because of its high PL content, current krill oil compositions' will not be a major fat source, but rather complimentary to other oils present when fat is used to meet caloric requirements. At present, there are a number of mixed-oil emulsions (e.g., soybean-MCT oils, soybean-olive oils, soybean-MCT-fish oils, soybean MCT-olive-fish oils), where krill oil might be added in small amounts as a means of achieving a unique modified oil mixture. Alternatively, chemical modifications of krill oil may allow greater utility as a daily caloric source.

According to another exemplary aspect, a method of parenterally administering a composition is provided, the method comprising parenterally administering to a person a composition containing krill oil in a parenteral oil-in-water emulsion as a specific source of omega-3 or n3 fatty acids, EPA and DHA. In some patients, for example, those requiring long-term parenteral nutrition support, the chronic provision of a modest amount of EPA and DHA in existing nutrition support regimens could favorably influence the otherwise inevitable development of end-stage liver disease over long periods of time. Alternatively, chemical modifications of krill oil may allow greater utility as a source of n3-FAs.

According to another exemplary aspect, a method of parenterally administering a composition is provided, the method comprising parenterally administering to a person a composition comprising krill oil in a parenteral oil-in-water emulsion as a source of n3-FAs to meet essential fatty acids requirements, and/or a daily caloric source of lipids in conjunction with other oils present, and/or a specific source of omega-3 or n3 fatty acids, EPA and DHA, and/or as an alternative surfactant to egg lecithin or in combination with egg lecithin to improve the physical stability of the emulsion. Alternatively, chemical modifications of krill oil may allow greater utility to meet these multiple uses.

According to another exemplary aspect, a method of parenterally administering a composition is provided, the method comprising parenterally administering to a person a composition comprising krill oil in a parenteral oil-in-water emulsion as an alternative and economically viable source of n3-FAs instead of conventional fish-derived sources. That is, as fish populations decline, krill populations will remain plentiful, and therefore they could become the principal source of omega-3 fatty acids, and thereby allow fish stocks to be replenished accordingly. Thus, purification and chemical separation of the n3-FAs and re-esterification to, for examples, ethyl esters, phospholipids and/or triglyceride molecules would be possible from a single marine oil source for multiple dosage forms.

As already described herein, exemplary emulsions can have various final compositions and characteristics depending on the specific application of the emulsion (composition). In an exemplary embodiment, the emulsion can be in compliance with the specifications set forth in United States Pharmacopoeia (USP) Chapter <729> entitled "Globule Size Distribution in Lipid Injectable Emulsions" (United States Pharmacopoeia, 2012), the content of which are incorporated herein by reference. The two exemplary globule size limits include: 1) the intensity-weighted mean droplet size that is less than 500 nm obtained by dynamic light scattering at 25° C.; and 2) the volume-weighted percent of fat greater than five micrometers or $PFAT_5$ that is less than 0.05% obtained by light extinction employing single-particle optical sensing methods.

The emulsion can have any suitable physical and chemical characteristics such as droplet size, and pH, free fatty acids, etc, as described in the USP monograph entitled "Lipid Injectable Emulsions" (United States Pharmacopoeia, 2012). For example, the emulsion can possess physical characteristics which facilitate its use in parenteral administration applications. In an exemplary embodiment, an emulsion can have a mean droplet size of, for example, less than 500 nm, or less than 350 nm, or less than 250 nm, or less than 240 nm or from 150 to 350 nm, such as 200 to 320 or 210 to 250 or 230 to 240 nm. In an exemplary embodiment, an emulsion can have a $PFAT_5$ value of less than 0.05%.

While various embodiments are described herein, it will be appreciated that variations, modifications and other changes in form and detail may be made without departing from the spirit and scope of the disclosure. Such variations and modifications are to be considered within the purview and scope of the disclosure as defined by the appended claims. The unique combination of omega-3 fatty acids, as attached to phospholipids in selected concentrations, presents a novel opportunity for constructing safe parenteral dosage forms for specific medical and pharmaceutical uses not obtainable with conventional omega-3 fatty acids-containing oils as triglycerides and/or ethyl esters.

TABLE 1

20% Oil-in-Water Krill Oil-Containing Emulsion Examples

| *PHARMACEUTICAL INGREDIENT | SAMPLE CONCENTRATION | RANGE OF CONCENTRATIONS |
|---|---|---|
| Krill Oil | 40 g/L | 12 to 200 g/L |
| Total Phospholipids | 45% w/w | 20 to 60% w/w |
| Total Triglycerides | 30% w/w | 15 to 45% w/w |

TABLE 1-continued

20% Oil-in-Water Krill Oil-Containing Emulsion Examples

| *PHARMACEUTICAL INGREDIENT | SAMPLE CONCENTRATION | RANGE OF CONCENTRATIONS |
|---|---|---|
| Sum of n3-FA | 35% w/w | 20 to 60% w/w |
| EPA (20:5n3) | 9 g/L | 1.6 to 80 g/L |
| DHA (22:6n3) | 5 g/L | 0.8 to 40 g/L |
| AA (20:4n6) | 0.2 g/L | 0.06 to 1.0 g/L |
| astaxanthin | 0.04 g/L | 0.012 to 0.2 g/L |
| Fish Oil | 100 g/L | 0 to 180 g/L |
| Sum of n3-FA | 45% w/w | ≥45% w/w |
| EPA (20:5n3) | 30 g/L | 0 to 54 g/L |
| DHA (22:6n3) | 15 g/L | 0 to 27 g/L |
| AA (20:4n6) | 0.5 g/L | 0 to 0.9 g/L |
| Total n3-FA | 59 g/L | 2.4 to 120 g/L |
| Total n6-FA | 0.7 g/L | 0.06 to 1.0 g/L |
| MCT Oil | 60 g/L | 0 to 100 g/L |
| Approved Pharmaceutical Excipients | | |
| Glycerol | 22.5 g/L | 20 to 25 g/L |
| Egg Phospholipids | 0 g/L | 0 to 18 g/L |
| Sodium Oleate | 2.5 g/L | 0 to 5 g/L |
| α-tocopherol | 0.2 g/L | 0 to 1 g/L |
| Sterile Water for Inj. | q.s. ad 1000.0 | Fixed |

TABLE 2

Examples of Modified Krill Oil Compositions, % w/w

| $EPA^1$ | $DHA^2$ | Total $n3FA^3$ | Total $PL^4$ | PL-$n3FA^5$ | Total $TG^6$ | TG-$n3FA^7$ |
|---|---|---|---|---|---|---|
| 30 | 15 | 45 | 10 | 20 | 70 | 80 |
| 30 | 15 | 45 | 20 | 30 | 60 | 70 |
| 30 | 15 | 45 | 30 | 40 | 50 | 60 |
| 30 | 15 | 45 | 40 | 50 | 40 | 50 |
| 30 | 15 | 45 | 50 | 60 | 30 | 40 |
| 30 | 15 | 45 | 60 | 70 | 20 | 30 |
| 30 | 15 | 45 | 70 | 80 | 10 | 20 |
| 40 | 20 | 60 | 10 | 20 | 70 | 80 |
| 40 | 20 | 60 | 20 | 30 | 60 | 70 |
| 40 | 20 | 60 | 30 | 40 | 50 | 60 |
| 40 | 20 | 60 | 40 | 50 | 40 | 50 |
| 40 | 20 | 60 | 50 | 60 | 30 | 40 |
| 40 | 20 | 60 | 60 | 70 | 20 | 30 |
| 40 | 20 | 60 | 70 | 80 | 10 | 20 |
| 15 | 30 | 45 | 10 | 20 | 70 | 80 |
| 15 | 30 | 45 | 20 | 30 | 60 | 70 |
| 15 | 30 | 45 | 30 | 40 | 50 | 60 |
| 15 | 30 | 45 | 40 | 50 | 40 | 50 |
| 15 | 30 | 45 | 50 | 60 | 30 | 40 |
| 15 | 30 | 45 | 60 | 70 | 20 | 30 |
| 15 | 30 | 45 | 70 | 80 | 10 | 20 |
| 20 | 40 | 60 | 10 | 20 | 70 | 80 |
| 20 | 40 | 60 | 20 | 30 | 60 | 70 |
| 20 | 40 | 60 | 30 | 40 | 50 | 60 |
| 20 | 40 | 60 | 40 | 50 | 40 | 50 |
| 20 | 40 | 60 | 50 | 60 | 30 | 40 |
| 20 | 40 | 60 | 60 | 70 | 20 | 30 |
| 20 | 40 | 60 | 70 | 80 | 10 | 20 |

[1]EPA = eicosapentaenoic acid (20:5n3)
[2]DHA = docosapentaenoic acid (22:6n3)
[3]Total n3FA = total omega-3 or n3 fatty acids
[4]Total PL = total phospholipids
[5]PL-n3FA = amount of omega-3 fatty acids in phospholipids
[6]Total TG = total triglycerides
[7]TG-n3FA = amount of omega-3 fatty acids in triglycerides

TABLE 3

Examples of Krill oil as a Surfactant or Co-Surfactant, 30% PL

| Krill Oil (g) | Egg Phospholipids (g) |
|---|---|
| 0 | 12.0 |
| 1 | 11.7 |
| 2 | 11.4 |
| 3 | 11.1 |
| 4 | 10.8 |
| 5 | 10.5 |
| 6 | 10.2 |
| 7 | 9.9 |
| 8 | 9.6 |
| 9 | 9.3 |
| 10 | 9.0 |
| 11 | 8.7 |
| 12 | 8.4 |
| 13 | 8.1 |
| 14 | 7.8 |
| 15 | 7.5 |
| 16 | 7.2 |
| 17 | 6.9 |
| 18 | 6.6 |
| 19 | 6.3 |
| 20 | 6.0 |
| 21 | 5.7 |
| 22 | 5.4 |
| 23 | 5.1 |
| 24 | 4.8 |
| 25 | 4.5 |
| 26 | 4.2 |
| 27 | 3.9 |
| 28 | 3.6 |
| 29 | 3.3 |
| 30 | 3.0 |
| 31 | 2.7 |
| 32 | 2.4 |
| 33 | 2.1 |
| 34 | 1.8 |
| 35 | 1.5 |
| 36 | 1.2 |
| 37 | 0.9 |
| 38 | 0.6 |
| 39 | 0.3 |
| 40 | 0 |

TABLE 4

Examples of Krill Oil (30% PL) as an Oil-in-Water Emulsion

| Krill Oil* | | Fish Oil** | | MCT | Egg Phospho- | Total |
|---|---|---|---|---|---|---|
| g/L | n3-FAs, g/L | g/L | n3-FAs, g/L | Oil g/L | lipids g/L | n3-FA, g g/L |
| colspan Assumes LipOmega-3 MCT 90/10 (marine oil = fish oil plus krill oil by weight) | | | | | | |
| 40 | 8.0 | 180 | 81.0 | 20 | 0 | 89.0 |
| 30 | 6.0 | 180 | 81.0 | 20 | 3 | 87.0 |
| 20 | 4.0 | 180 | 81.0 | 20 | 6 | 85.0 |
| 10 | 2.0 | 180 | 81.0 | 20 | 9 | 83.0 |
| Assumes LipOmega-3 MCT 90/10 (marine oil = fish oil minus krill oil by weight) | | | | | | |
| 40 | 8.0 | 140 | 63.0 | 16 | 0 | 71.0 |
| 30 | 6.0 | 150 | 67.5 | 16.5 | 3 | 73.5 |
| 20 | 4.0 | 160 | 72.0 | 17 | 6 | 76.0 |
| 10 | 2.0 | 170 | 76.5 | 19 | 9 | 78.5 |
| Assumes LipOmega-3 MCT 50/50 (marine oil = fish oil plus krill oil by weight) | | | | | | |
| 40 | 8.0 | 100 | 45.0 | 100 | 0 | 53.0 |
| 30 | 6.0 | 100 | 45.0 | 100 | 3 | 51.0 |
| 20 | 4.0 | 100 | 45.0 | 100 | 6 | 49.0 |
| 10 | 2.0 | 100 | 45.0 | 100 | 9 | 47.0 |
| Assumes LipOmega-3 MCT 50/50 (marine oil = fish oil minus krill oil by weight) | | | | | | |
| 40 | 8.0 | 80 | 36.0 | 80 | 0 | 44.0 |
| 30 | 6.0 | 85 | 38.3 | 85 | 3 | 44.3 |
| 20 | 4.0 | 90 | 40.5 | 90 | 6 | 44.5 |
| 10 | 2.0 | 95 | 42.8 | 95 | 9 | 44.8 |

*Assumes: Krill Oil = 30% PL (12 g/L of egg PL = 40 g/L krill PL), minimum EPA + DHA = 20%;
**Fish Oil: meets requirements of Pharm Eur Monograph 1352, minimum EPA + DHA = 45%

TABLE 5

Examples of Krill Oil (50% PL) as an Oil-in-Water Emulsion

| Krill Oil* | | Fish Oil** | | MCT | Egg Phospho- | Total |
|---|---|---|---|---|---|---|
| g/L | n3-FAs, g/L | g/L | n3-FAs, g/L | Oil g/L | lipids g/L | n3-FA, g g/L |
| Assumes LipOmega-3 MCT 90/10 (marine oil = fish oil plus krill oil by weight) | | | | | | |
| 24 | 4.8 | 180 | 81.0 | 20 | 0 | 85.8 |
| 18 | 3.6 | 180 | 81.0 | 20 | 3 | 84.6 |
| 12 | 2.4 | 180 | 81.0 | 20 | 6 | 83.4 |
| 6 | 1.2 | 180 | 81.0 | 20 | 9 | 82.2 |
| Assumes LipOmega-3 MCT 90/10 (marine oil = fish oil minus krill oil by weight) | | | | | | |
| 24 | 4.8 | 156 | 70.2 | 16 | 0 | 75.0 |
| 18 | 3.6 | 162 | 72.9 | 16.5 | 3 | 76.5 |
| 12 | 2.4 | 168 | 75.6 | 17 | 6 | 78.0 |
| 6 | 1.2 | 174 | 78.3 | 19 | 9 | 79.5 |
| Assumes LipOmega-3 MCT 50/50 (marine oil = fish oil plus krill oil by weight) | | | | | | |
| 24 | 4.8 | 100 | 45.0 | 100 | 0 | 49.8 |
| 18 | 3.6 | 100 | 45.0 | 100 | 3 | 48.6 |
| 12 | 2.4 | 100 | 45.0 | 100 | 6 | 47.4 |
| 6 | 1.2 | 100 | 45.0 | 100 | 9 | 46.2 |
| Assumes LipOmega-3 MCT 50/50 (marine oil = fish oil minus krill oil by weight) | | | | | | |
| 24 | 4.8 | 76 | 34.2 | 80 | 0 | 39.0 |
| 18 | 3.6 | 82 | 36.9 | 85 | 3 | 40.5 |
| 12 | 2.4 | 88 | 39.6 | 90 | 6 | 42.0 |
| 6 | 1.2 | 94 | 42.3 | 95 | 9 | 43.5 |

*Assumes: Krill Oil = 50% PL (12 g/L of egg PL = 24 g/L krill PL), minimum EPA + DHA = 20%;
**Fish Oil: meets requirements of Pharm Eur Monograph 1352, minimum EPA + DHA = 45%

TABLE 6

Stability of Lipid Injectable Emulsions of Varying
Oil Composition Under Stress Conditions
Stress Conditions for Lipid Injectable Emulsions
20% oil-in-water emulsion

| Oil(s) | Total Samples | $PFAT_5 >$ 0.05% | Peak $PFAT_5$ | % Fail |
|---|---|---|---|---|
| Plant Oil-1 | | | | |
| Stress-1* | 32 | 0 | 0.043 | 0 |
| Stress-2* | 32 | 0 | 0.044 | 0 |
| Stress-3* | 32 | 0 | 0.043 | 0 |
| Stress-4* | 32 | 0 | 0.046 | 0 |
| Plant Oil-2 | | | | |
| Stress-1 | 48 | 0 | 0.029 | 0 |
| Stress-2 | 48 | 0 | 0.033 | 0 |
| Stress-3 | 48 | 0 | 0.046 | 0 |
| Stress-4 | 48 | 0 | 0.031 | 0 |
| Plant + 10% Marine Oil | | | | |
| Stress-1 | 48 | 0 | 0.026 | 0 |
| Stress-2 | 48 | 5 | 0.071 | 10 |
| Stress-3 | 48 | 0 | 0.038 | 0 |
| Stress-4 | 48 | 5 | 0.065 | 10 |
| Plant + 50% Marine Oil | | | | |
| Stress-1 | 20 | 7 | 0.212 | 35 |
| Stress-2 | 20 | 12 | 0.171 | 60 |
| Stress-3 | 20 | 3 | 0.290 | 15 |
| Stress-4 | 20 | 9 | 0.299 | 45 |
| Plant + 70% Marine Oil | | | | |
| Stress-1 | 20 | 10 | 0.107 | 50 |
| Stress-2 | 20 | 12 | 0.254 | 60 |
| Stress-3 | 20 | 4 | 0.182 | 20 |
| Stress-4 | 20 | 6 | 0.148 | 30 |
| Plant + 90% Marine Oil | | | | |
| Stress-1 | 40 | 21 | 0.192 | 53 |
| Stress-2 | 40 | 22 | 0.305 | 55 |
| Stress-3 | 40 | 11 | 0.272 | 28 |
| Stress-4 | 40 | 25 | 0.516 | 63 |

*Applied as per: U.S. Pat. No. 7,150,996 (Dec. 19, 2006)

Exemplary pharmaceutical compositions of the invention comprising emulsions 1 to 3 shown in Tables 7 to 9

TABLE 7

Emulsion 1

| Component | Amount per 1000 ml |
|---|---|
| Medium chain triglyceride[a] | 100 g |
| Omega-3 fatty acid triglyceride[b] | 100 g |
| Phospholipid obtained from krill | 12 g |
| Glycerin | 25 g |
| Sodium oleate | 0.3 g |
| alpha-tocopherol | 0.2 g |
| NaOH | max. 0.06 g |
| water | ad 1000 ml |

TABLE 8

Emulsion 2

| Component | Amount per 1000 ml |
|---|---|
| Medium chain triglyceride[a] | 60 g |
| Omega-3 fatty acid triglyceride[b] | 140 g |
| Phospholipid obtained from krill | 12 g |
| Glycerin | 25 g |
| Sodium oleate | 0.3 g |
| alpha-tocopherol | 0.2 g |

TABLE 8-continued

Emulsion 2

| Component | Amount per 1000 ml |
|---|---|
| NaOH | max. 0.06 g |
| water | ad 1000 ml |

TABLE 9

Emulsion 3

| Component | Amount per 1000 ml |
|---|---|
| Medium chain triglyceride[a] | 20 g |
| Omega-3 fatty acid triglyceride[b] | 180 g |
| Phospholipid obtained from krill | 12 g |
| Glycerin | 25 g |
| Sodium oleate | 0.3 g |
| alpha-tocopherol | 0.2 g |
| NaOH | max. 0.06 g |
| water | ad 1000 ml |

[a]Medium chain triglyceride (MCT) [triglyceride obtained from esterification of glycerine with medium chain fatty acids;
minimum 95% of saturated fatty acids with 8 and 10 carbon atoms;
Composition of the fatty acid fraction:
caproic acid: maximum 2.0%
caprylic acid: 50.0 to 80.0%,
capric acid: 20.0 to 50.0%,
lauric acid: maximum 3.0% and
myristic acid: maximum 1.0%
[b]Fish oil derived Omega-3 fatty acid triglyceride in accordance with the European Pharmacopeia 1352: Mixture of mono-, di- and triesters of omega-3 acids with glycerol containing mainly triesters and obtained either by esterification of concentrated and purified omega-3 acids with glycerol or by transesterification of the omega-3 acid ethyl esters with glycerol. The origin of the omega-3 acids is the body oil from fatty fish species coming from families like Engraulidae, Carangidae, Clupeidae, Osmeridae, Salmonidae and Scombridae. The content:
sum of the contents of the omega-3 acids EPA and DHA, expressed as triglycerides: minimum 45.0%
total omega-3 fatty acids, expressed as triglycerides: minimum 60.0%.

Examples of Potential Drugs which may be administered separately or simultaneously with the parenterally applicable pharmaceutical compositions of the invention, in particular the compositions reflected in Tables 7 to 9.

1. Antibiotics
  a. aminoglycosides
  b. amphotericin
  c. chloramphenicol
  d. ketoconazole
  e. macrolides
  f. quinolones
  g. tetracyclines
2. Antineoplastic Agents
  a. alkylating agents
  b. antimetabolites
  c. antimitotics platinum coordination complexes
3. Anti-Parkinson Agents
  a. levodopa
  b. pramipexole
  c. ropinirole
  d. rotigotine
  e. bromocriptine
4. Cardiovascular Agents
  a. adenosine
  b. amiodarone
  c. angiotensin converting enzyme (ACE) inhibitors
  d. flecainide
5. Diuretics
  a. loop diuretics
  b. potassium-sparing diuretics
  c. thiazides 6. Immunosuppressive Agents
    a. Azathioprine
    b. Cyclosporine
    c. Mycophenolate
    d. Tacrolimus
7. Non-Steroidal Anti-Inflammatory Drugs (NSAIDs)
    a. acetaminophen
    b. aspirin
    c. ibuprofen
    d. indomethacin
    e. ketorolac
8. Psychotropics
    a. haloperidol
    b. monoamine oxidase inhibitors
    c. phenothiazines
    d. serotonin reuptake inhibitors
    e. thioxanthines

REFERENCES

1. Bruheim I et al. Bioeffective krill oil compositions. Application Number 2008027403, Nov. 6, 2008.
2. Omega-3 Säuren-Triglyceride, 2005. Monograph 1352, German Pharmacopeia, Kommentar zur Ph. Eur. 5.0, 22 Lfg., pp. 1-4
3. Driscoll D F, Ling P R, Bistrian B R. Pharmacopeial compliance of fish oil-containing parenteral lipid emulsion mixtures: Globule size distribution (GSD) and fatty acid analyses. Int J Pharm. 2009; 379(1):125-30
4. Winther B, Hoem N, Berge K, Reubsaet L. Elucidation of phosphatidylcholine composition in krill oil extracted from Euphausia superba. Lipids 2010; 45:25-36
5. Driscoll D F, Adolph M, Bistrian B R. Lipid emulsions in parenteral nutrition. In Parenteral Nutrition. Rombeau J. L., Rolandelli R. (eds): W. B. Saunders Company, Philadelphia, Pa., 2001, pp. 35-59
6. Gordon B R, Parker T S, Levine D M et al. Neutralization of endotoxin by phospholipids emulsion in healthy volunteers. J Infect Dis 2005; 191:1515-1522
7. Dellenger P, Tomayko J F, Angus D C et al. Efficacy and safety of a phospholipids emulsion (GR270773) in gram-negative severe sepsis: Results of a phase II multicenter, randomized, placebo-controlled, dose-finding clinical trial. Crit Care Med 2009; 37:29-38
8. Lee J S, Pinnamaneni S K, Eo S J et al. Saturated, but not n-6 polyunsaturated, fatty acids induce insulin resistance: role of intramuscular accumulation of lipid metabolites. J Appl Phsyiol 2006; 100:1467-74
9. Driscoll D F, Nehne J, Peterss H et al. The influence of medium-chain triglycerides on the stability of all-in-one formulations. Int J Pharm 2002; 240:1-10
10. Larsen B, Beerhalter U, Biedler A et al. Less pain on injection by a new formulation of propofol? A comparison with propofol LCT. Anaesthesist 2001; 50: 842-45
11. Rangel-Fausto M S, Pittet D, Costigan M et al. The natural history of systemic inflammatory response syndrome (SIRS): A prospective study. JAMA 1995; 273: 117-23
12. Jones L D, Castleberry M W, Canham J E, King N W. Toxicity testing of fat emulsions for intravenous administration. Am J Clin Nutr 1965; 16:62-67
13. Turner-Lawrence D E, Kerns W. Intravenous fat emulsion: a potential novel antidote. J Med Toxicol 2008; 4:109-14
14. Hiller D B, DiGregorio G, Kelly K et al. Safety of high volume lipid emulsion infusion. Reg Anesth Pain Med 2010; 35:140-44
15. Bistrian B R. Clinical aspects of essential fatty acid metabolism: Jonathan Rhoads Lecture. J Parenter Enter Nutr 2003; 27:168-75
16. de Meijer V E, Gura K M, Le H D et al. Fish oil-based lipid emulsions prevent and reverse parenteral nutrition-associated liver disease: The Boston experience. J Parenter Enter Nutr 2009; 33:541-47.
17. Le H D, deMeijer V E, Zurakowski D et al. Parenteral fish oil as monotherapy improves lipid profiles in children with parenteral nutrition-associated liver disease. J Parenter Enter Nutr 2010; 34:477-8

The invention claimed is:

1. A parenterally applicable pharmaceutical composition, comprising an oil-in-water emulsion comprising a phospholipid obtained from a marine crustacean and a drug,
    wherein the phospholipid obtained from a marine crustacean is present in an amount effective to solubilize the drug,
    wherein the drug is selected from the group consisting of:
        an antibiotic selected from the group consisting of an aminoglycoside, amphotericin, chloramphenicol, ketoconazole, macrolide, quinolone and tetracycline;
        an antineoplastic agent selected from the group consisting of an alkylating agent, antimetabolite, and antimitotic platinum coordination complex;
        a cardiovascular agent selected from the group consisting of an adenosine, amiodarone, angiotensin converting enzyme (ACE) inhibitor and flecainide;
        a diuretic selected from the group consisting of a loop diuretic, potassium-sparing diuretic and thiazide;
        an immunosuppressive agent selected from the group consisting of an azathioprine, cyclosporine, mycophenolate and tacrolimus;
        a psychotropic selected from the group consisting of haloperidol, monoamine oxidase inhibitor, phenothiazine, serotonin reuptake inhibitor and thioxanthine;
        a non-steroidal anti-inflammatory drug selected from the group consisting of an acetaminophen, aspirin, ibuprofen, indomethacin and ketorolac; and
        a pharmaceutically acceptable salt thereof,
    wherein the phospholipid obtained from a marine crustacean is a phospholipid obtained from krill,
    wherein the oil phase of the oil-in-water emulsion consists of a fish oil, a medium chain triglyceride oil, and the drug, wherein the phospholipid obtained from krill functions as a surfactant of the oil-in-water emulsion.

2. The composition of claim 1, wherein the composition is suitable for treatment of endotoxicosis during sepsis.

3. The composition of claim 1, wherein the composition is suitable for mitigating adverse drug effects to vital organs involving inflammation, oxidative stress, immune modulation and/or ischemic events.

4. The composition of claim 1, wherein the composition is suitable for treatment of a person having toxic blood levels of highly lipophilic drugs.

5. The composition according to claim 1, wherein the composition comprises the phospholipid obtained from krill in an amount ranging from 0.05 g/l to 100 g/l, based on the total pharmaceutical composition.

6. The composition according to claim 1, wherein the phospholipid obtained from a marine crustacean comprises omega-3 fatty acid-containing phospholipids containing DHA in an amount of about 10 to about 20 wt.-%, based on the total weight of the fatty acid content of the phospholipids.

7. The composition according to claim 1, wherein the phospholipid obtained from krill comprises omega-3 fatty acid-containing phospholipids containing EPA in an amount of about 20 to about 40 wt.-%, based on the total weight of the fatty acid content of the phospholipids.

8. The composition according to claim 1, wherein the weight ratio of oil to water in the oil-and-water emulsion is from about 1:99 to about 20:80.

9. A pharmaceutical composition for parenteral administration composition according to claim 1 comprising
an omega-3-fatty acid component selected from the group consisting of omega-3-fatty acid triglycerides and omega-3-fatty acid ester.

10. A method, comprising administering the composition of claim 1 to a person, wherein the emulsion comprising the phospholipid obtained from krill and the drug are administered simultaneously.

11. A method, comprising administering the composition of claim 1 to a person, wherein the drug is suitable for treatment of toxic side effects of said drug.

12. A method, comprising administering the composition of claim 1 to a person in a manner that is effective to mitigate toxicity effects of said drug.

13. The pharmaceutical composition according to claim 1 wherein the composition comprises omega-3-fatty acid triglycerides and medium chain triglycerides (MCT).

14. The pharmaceutical composition according to claim 13 wherein the emulsion comprises 10 to 69 wt.-% MCT, based on the total amount of the oil component in the emulsion.

15. The pharmaceutical composition according to claim 1, wherein the fish oil comprises fish oil triglycerides in an amount of about 60% to about 90% based on the weight of the oil component; wherein the fish oil triglycerides comprise omega-3 fatty acids in an amount of at least 60%, based on the total weight of the fatty acids of the fish oil triglycerides; wherein the fish oil triglycerides comprise a total amount of EPA and DHA of at least 45%, based on the total weight of the fatty acids of the fish oil triglycerides; and the medium-chain triglyceride oil is from about 10% to about 40% based on the weight of the oil component.

16. The pharmaceutical composition according to claim 1, wherein the drug is a material that damages a vital organ when the material is not simultaneously administered with at least one omega-3 fatty acid.

17. The pharmaceutical composition according to claim 1, wherein the drug is present in an amount of about 0.005% to about 1.5%, based on the weight of the composition.

18. The pharmaceutical composition according to claim 1, wherein the drug is a Non-Steroidal Anti-Inflammatory Drug selected from the group consisting of acetaminophen, aspirin, ibuprofen, indomethacin, ketorolac and pharmaceutical acceptable salts and derivatives thereof for treatment of pain or swelling or redness or fever or inflammation.

19. The pharmaceutical composition according to claim 18, wherein the drug is ketorolac or a pharmaceutical acceptable salt of ketorolac.

20. A method, comprising administering the pharmaceutical composition according to claim 19 to a person by daily parenteral administration to administer ketorolac tromethamine in a single dose of more than 60 mg or in multiple doses of more than 120 mg/day.

21. The pharmaceutical composition according to claim 18, wherein the drug is indomethacin or a pharmaceutical acceptable salt of indomethacin for treatment for closing a hemodynamically significant patent ductus arteriosus in premature infants weighing between 500 g and 1750 g.

22. A method, comprising administering the pharmaceutical composition according to claim 21 to a premature infant weighing between 500 g to 1750 g by parenteral administration of three intravenous courses at 12 to 24 hour intervals with the first dose of more than 0.2 mg/kg.

23. The pharmaceutical composition according to claim 1, wherein the drug is acetaminophen for treatment of pain and/or fever.

24. A method, comprising administering the pharmaceutical composition according to claim 23 to a patient weighing ≥50 kg by daily parenteral administration to administer acetaminophen in a single dose of more than 1000 mg or in multiple doses of more than 4000 mg/day.

25. A method, comprising administering the pharmaceutical composition according to claim 23 to a patient weighing less than 50 kg by daily parenteral administration to administer acetaminophen in a single dose of more than 15 mg/kg of body weight or in multiple doses of more than 75 mg/kg/day.

26. The pharmaceutical composition according to claim 1, wherein the drug is amiodarone or a pharmaceutical acceptable salt amiodarone.

27. A method, comprising administering the pharmaceutical composition according to claim 26 to a person by daily parenteral administration to administer amiodarone hydrochloride in a dose over the first 24 hours of more than 1000 mg; and more than 720 mg as maintenance infusion over 24 hours.

28. The pharmaceutical composition according to claim 1, wherein the at least one drug is an antineoplastic agent for reducing the toxicity to vital organs.

29. The pharmaceutical composition according to claim 1, wherein the at least one drug is an antineoplastic agent for enhancing the toxicity against tumor cells.

30. The pharmaceutical composition according to claim 1, wherein the at least one drug is an antineoplastic agent for simultaneously reducing the toxicity of the drug and enhancing its toxicity against tumor cells.

31. The composition according to claim 1 wherein the composition comprises the phospholipid obtained from the marine crustacean in an amount ranging from 0.1 to 50 g/l, based on the total pharmaceutical composition, wherein the marine crustacean is krill.

32. The composition according to claim 1, wherein the composition comprises the phospholipid obtained from the marine crustacean in an amount ranging from 0.5 to 30 g/l, based on the total pharmaceutical composition, wherein the marine crustacean is krill.

33. The composition according to claim 1, wherein the composition comprises the phospholipid obtained from the marine crustacean in an amount ranging from 5 to 20 g/l, based on the total pharmaceutical composition.

34. A method of parenterally administering a composition, the method comprising parenterally administering to a person a composition according to claim 1.

35. The method according to claim 34, wherein the phospholipid obtained from krill is present in an amount effective to increase the physical stability of the emulsion, in comparison with the physical stability of an identical emulsion containing egg lecithin in place of the phospholipid obtained from krill.

36. The method according to claim 34, wherein the phospholipid obtained from krill is present in an amount effective to increase the chemical stability of the emulsion, in comparison with the chemical stability of an identical emulsion containing alpha-tocopherol in place of the phospholipid obtained from krill.

37. The method according to claim 34, wherein the composition comprises a highly lipophilic drug, and the phospholipid obtained from krill is present in an amount effective to solubilize the highly lipophilic drug.

38. The method according to claim 34, wherein the composition comprises n3 fatty acids in an amount effective to mitigate adverse drug effects to vital organs involving inflammation, oxidative stress, immune modulation and/or ischemic events.

39. The method according to claim 34, wherein the method is a method for treating endotoxicosis during severe sepsis.

40. The method according to claim 34, wherein the method is a method for treating a person having toxic blood levels of highly lipophilic drugs.

41. The method according to claim 34, wherein the composition is substantially free of egg lecithin.

42. The method according to claim 34, wherein the phospholipid obtained from krill contains EPA and DHA.

43. The method according to claim 34, wherein the composition is substantially free of n3-FAs from a fish-derived source.

44. The method according to claim 34, wherein the total phospholipid content is 10 to 70% w/w, wherein 20 to 80% of the total n3-FA content is present in the phospholipid, wherein the total triglyceride content is from 10 to 70% w/w, wherein 20 to 80% of the total n3-FA content is present in the triglyceride, and wherein the total n3-FA content is from 45 to 60% w/w.

45. A method for parenterally administering a composition, the method comprising parenterally administering to a person the composition according to claim 1, wherein after administration said phospholipid binds with an endotoxin.

46. A method for parenterally administering a composition, the method comprising parenterally administering to a person the composition according to claim 1, wherein after administration said phospholipid binds with a highly lipophilic drug.

* * * * *